United States Patent

Subramanian et al.

[11] Patent Number: 5,808,003
[45] Date of Patent: *Sep. 15, 1998

[54] POLYAMINOCARBOXYLATE CHELATORS

[75] Inventors: Ramaswamy Subramanian, Frederick, Md.; James Colony, Seattle, Wash.

[73] Assignee: PerImmune Holdings, Inc., Rockville, Md.

[ * ] Notice: The term of this patent shall not extend beyond the expiration date of Pat. No. 5,292,868.

[21] Appl. No.: 666,296

[22] PCT Filed: Jan. 5, 1995

[86] PCT No.: PCT/US95/00068

§ 371 Date: Sep. 18, 1996

§ 102(e) Date: Sep. 18, 1996

[87] PCT Pub. No.: WO95/18832

PCT Pub. Date: Jul. 13, 1995

Related U.S. Application Data

[63] Continuation-in-part of Ser. No. 044,875, Apr. 8, 1993, Pat. No. 5,292,868, which is a continuation of Ser. No. 720,277, Jun. 24, 1991, abandoned, which is a continuation of Ser. No. 438,558, Nov. 17, 1989, abandoned, which is a continuation-in-part of Ser. No. 358,917, May 26, 1989, abandoned.

[51] Int. Cl.[6] .......................... C07K 16/00; C07K 17/00; A61K 51/08; C07C 331/28
[52] U.S. Cl. .................. 530/391.5; 436/504; 436/545; 436/546; 530/391.1; 530/391.3; 530/405; 530/409; 540/460; 558/17; 562/434; 562/437; 562/450; 564/196; 564/367; 564/368; 564/369
[58] Field of Search .................. 530/391.1, 391.3, 530/391.5, 405, 409; 562/434, 437, 450; 564/159, 196, 367, 368, 369; 558/17; 540/460; 436/504, 545, 548

[56] References Cited

U.S. PATENT DOCUMENTS

| | | | |
|---|---|---|---|
| 4,678,667 | 7/1987 | Meares et al. | 424/1.53 |
| 4,885,363 | 12/1989 | Tweedle et al. | 540/465 |
| 5,057,302 | 10/1991 | Johnson et al. | 424/117 |
| 5,101,041 | 3/1992 | Troutner et al. | 548/518 |
| 5,281,704 | 1/1994 | Love et al. | 540/465 |
| 5,292,868 | 3/1994 | Subramanian et al. | 530/391.5 |
| 5,364,613 | 11/1994 | Sieving et al. | 424/9 |
| 5,488,126 | 1/1996 | Subramanian et al. | 557/17 |
| 5,650,133 | 7/1997 | Carvalho et al. | 424/1.65 |

FOREIGN PATENT DOCUMENTS

| | | |
|---|---|---|
| 0238196 | 9/1987 | European Pat. Off. |
| 0296522 | 12/1988 | European Pat. Off. |
| WO84/03698 | 9/1984 | WIPO |
| WO86-06605 | 11/1986 | WIPO |
| WO88/01178 | 2/1988 | WIPO |
| WO90/14881 | 12/1990 | WIPO |

OTHER PUBLICATIONS

Moi et al., *Inorganic Chemistry*, 26(21) :3458–3463, 1987.

Brechbeil et al., *Inorganic Chemistry*, 25:2772–2781, 1986.

Subramanian et al., *Bioconjugate Chemistry*, 3, 1992.

Lindmo et al., *J. Immunol. Meth.*, 72(1) :77–79, 1984.

M. Pillai et al., *Nucl. Med. Biol.*, 17:4:419–426, 1990.

*Primary Examiner*—Ponnathapura Achutamurthy
*Attorney, Agent, or Firm*—William M. Blackstone

[57] ABSTRACT

A compound according to the formula:

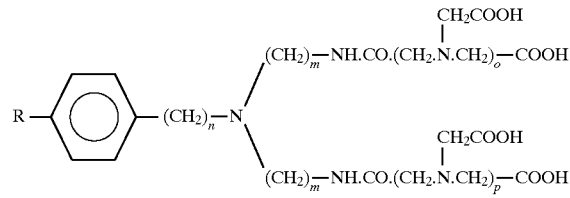

and conjugates thereof.

12 Claims, 5 Drawing Sheets where X=H; $-(CH_2)_l-NH_2$, where l=0 to 12; or $-(CH_2-NH-CH_2-CH_2-NH)_q-NH_2$, where q=0 to 12 m=2 to 12 n=0 to 12 and R= $-NCS$; $-NH-CO-CH_2-Br$ or $-N_2Cl$.

LiLo2'

HETA2

VIII →(Pd/C, H₂)→

IX

X

←(i) CSCl₂  ii) HCl)—

POLYAMINOCARBOXYLATE CHELATORS

This application is a continuation-in-part of U.S. application Ser. No. 08/044,875, filed Apr.8, 1993, U.S. Pat. No. 5,292,868 which is a continuation of U.S. Ser. No. 07/720,277, filed Jun. 24, 1991, now abandoned, which is a continuation of U.S. Ser. No. 07/438,558, filed Nov. 17, 1989, now abandoned, which is a continuation-in-part of U.S. Ser. No. 07/358,917, filed May 26, 1989, now abandoned, all of which are included herein by reference.

This invention relates to new chelating agents for attaching metal ions to peptides and proteins such as albumin, transferrin, antibodies and antibody fragments.

BACKGROUND OF THE INVENTION

Attachment of metal ions to proteins leads to several useful products. These include fluorescent, radioactive and paramagnetic metal ions attached proteins that can be used as probes in vivo in biological systems and in vitro in analytical systems, such as radioimmunoassays. For example, attachment of radionuclides to monoclonal antibodies that recognize tumor associated antigens provides radioimmunoconjugates useful for cancer diagnosis and therapy. The monoclonal antibodies are used as carriers of desired substances to specific sites in-vivo. Several chelating agents, such as diethylenetriaminepentaacetic acid (DTPA), ethylenediaminetetraacetic acid (EDTA) and macrocyclics, have been reported to form stable complexes when attached to proteins. However, kinetic instability of the radioimmunoconjugate or the chelate under physiological conditions results in the breakdown of these complexes. Despite several attempts to modify the mode of binding, structure of chelate and etc., in vivo administration of such radioimmunoconjugates has resulted in accumulation of radioactivity in non-target tissues, particularly in the liver. Hence, there is an obvious need for new chelating agents for binding radiometals to antibodies to form complexes that do not disassociate when administered to a patient.

It is an object of this invention to provide a new set of chelating agents for attaching metal ions to proteins and thereby provide an aqueous solution containing antibody-chelate conjugate that is stable in vivo.

It is further an object of this invention to provide a set of chelating agents to bind a variety of metal ions, including In, Y, Gd, Tb, Eu, Cu, Co, Sm, Rh, Ru, Re, Bi, Tl, Tc, Fe, Pb and Ba, Lu, as well other actinides, lanthanides and transition metal ions.

It is further an object of this invention to synthesize new chelation structures useful for attaching metal ions to proteins, including monoclonal antibodies.

It is another object of this invention to obtain versatile chelating agents that are not only suitable for binding to low molecular weight proteins, such as albumin and IgG, but also to high molecular weight proteins, such as IgMs ($9 \times 10^5$) and lipoproteins ($2 \times 10^6$).

It is still another object of this invention to obtain an improved method for preparing metal chelate conjugated antibodies.

An additional object of this invention is to obtain chelation structures that provide a high metal ion concentration per antibody molecule without destroying the biological activity of the conjugated protein to a significant extent.

It is still another object of this invention to obtain fluorescent labeled proteins by attaching fluorescent/luminescent metal ions to protein-chelate conjugates.

It is further the object of this invention to obtain metal ion binding reagents that can be attached to chromatographic column materials such as polymers and gels, forming chelate affinity columns.

These and other objects are accomplished by one or more of the embodiments of the present invention.

Table 1 gives the percentage of indium(111) bound to 16.88-LiLo2' as a function of time of incubation in the presence of excess DTPA (indium-111.MoAb:DTPA= 1:>5000) at 37° C., as well as in phosphate buffered saline solution containing 1% HSA solution.

Table 2 represents the stability of 88BV59-HETA2.In (111) in several solutions: in the presence of excess of DTPA (indium-111.MoAb:DTPA=1:>5000) at 37° C., as well as in normal human serum, and in phosphate buffered saline solution containing 1% HSA solution.

SUMMARY OF THE INVENTION

This invention relates to a new family of polyaza macrocyclic reagents and polyaminocarboxylates. HETA2 and LiLo2' are two such polyaminocarboxylate type chelating agents suitable for attaching metals to proteins. Specifically, these compounds are useful for binding radiometals, such as indium-111, yttrium-90, technetium-99m, rhenium-186, rhenium-188, copper-64, copper-67, ruthenium-93, rhodium, gallodinium, samarium-153, bismuth-212, lead-213 and actinium-225, to proteins, such as monoclonal and polyclonal antibodies and fragments derived therefrom, oligonucleotides, polynucleotides, synthetic polymers and co-polymers.

DESCRIPTION OF THE PREFERRED EMBODIMENTS

Polyaminocarboxylates such as EDTA and DTPA have been used as chelators to bind metal ions such as copper, technetium, indium and yttrium. Macrocyclic reagents such as TETA (See for example Meares et al, U.S. Pat. No. 4,678,667 dated Jul. 7, 1987) have also been found to form stable radioimmunodiagnostic and therapeutic reagents suitable for in-vivo use for medical applications. We have discovered a new group of chelators wherein the polyaminocarboxylate branches are bound to a nitrogen, which, we believe, provides a stable structure when chelating metals. This invention comprises a new family of polyaza macrocyclic reagents and polyaminocarboxylates.

The new compounds according to the invention are useful for linking metals to amino acid sequences. The preferred use of these compounds is the preparation of radiometal labeled antibodies or antibody fragments for in-vivo immunodiagnostics or radioimmunotherapy. Other uses will be known to the skilled practitioner, for example, column purification. For the purposes of this invention, "metals" will refer to radiometals, non-radioactive metals and metal complexes and compounds that expose the metal ion for binding. The other side of the chelator will bind an amino acid sequence, which may be a peptide, polypeptide, protein, glycoprotein or a similar compound. The only limitation is that it be bound to the —NCS— group or other appropriate reactive moieties. For purposes of this invention, the term "polypeptide" will be used to include all of these compounds. The preferred "polypeptide" is an antibody or fragment. The chelator may be bound to a polypeptide through —CS—NH—,—CH$_2$—CO—NH— or —N—N— groups or through a direct bond.

Figure 1:
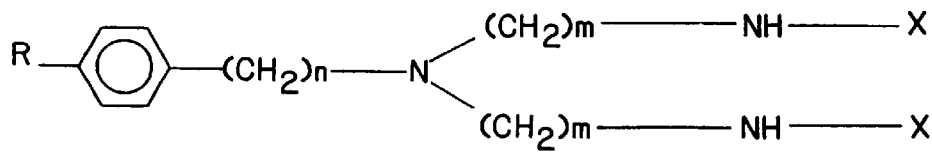
FIG. 1 Polyamine structure.

The polyaza macrocyclic compounds and polyaminocarboxylates of the invention can be prepared by derivatizing polyamines of the general formula shown in FIG. 1. The polyamine intermediate compounds can be prepared from starting materials such as (p-nitrophenyl)ethyl amine. These primary amines are carboxymethylated using bromoethylacetate or an equivalent reagent to obtain carboxymethylated amine derivatives which in turn can be converted to primary amines. These compounds are condensed with diethylenetriaminepentaacetic acid dianhydride using a method similar to the one described in Subramanian et al., Bioconjugate Chemistry, 3, 248–255 (1992). This sequence of reactions results in the bifunctional chelating agents such as HETA2 and LiLo2'. Varying the number of carbons in the methylene backbone (varying l,q, m and n) in the polyamine structure described above (FIG. 1) enables one to synthesize various bifunctional chelating agents according to the invention.

EXAMPLES

Synthesis of I (Diesteramine): 15 g of 4-nitrobenzyl-ethylamine.hydrochloride, 21 ml of ethylbromoacetate and 26 g of potassium carbonate were combined in 200 ml of acetonitrile and heated to reflux with strong stirring. The refluxing of the reaction mixture was performed overnight with continuous stirring. The reaction mixture was then cooled to room temperature and then filtered and rotoevaporated with additions of ethyl acetate. The product was run down a silica gel column (0.2% methanol in methylene chloride). Pure fractions were combined and rotoevaporated. Yield 16.5 g. IR (KBr pellet): 1742.9 cm$^{-1}$, 1600.2 cm$^{-1}$, 1519.5 cm$^{-1}$, 1346.3 cm$^{-1}$, 1189.8 cm$^{-1}$, 1030.4 cm$^{-1}$, 1H NMR (CDCl3): 1.3 (t, 6H), 3 (s,4H), 3.6 (s, 4H), 4.3 (q, 4H), 7.5 (d,2H), 8.3(d, 2H). Rf, 0.61 (0.1% methanol in methylene chloride).

Synthesis of II (Diesteramide): 14.3 g of disteramine (I) was dissolved in 500 ml of methanol and cooled in an ice bath. Ammonia gas was bubbled through the solution to the point of saturation, the solution was cooled in ice for _30 minutes and ammonia gas was bubbled through the solution again to the point of saturation. It was then placed in the refrigerator overnight (2°–8° C.). The solution was then concentrated down to _30 ml by evaporation. This resulted in a white precipitate, which was filtered off, rinsed with a small amount of methanol and dried. Yield was 6.1 g. The solution was diluted with methylene chloride and placed in the freezer (−25° C.), producing a crop of crystals of product. Yield was 4.6 g (9% total yield). IR (KBr pellet): 3382.9 cm$^{-1}$, 3263.2 cm$^{-1}$, 2832.5 cm$^{-1}$, 1652.8 cm$^{-1}$, 1513.8 cm$^{-1}$, 1343.7 cm$^{-1}$, 1136 cm$^{-1}$, 1H NMR (MeOD): 2.9 (s, 4H), 3.3 (s, 4H), 7.4 (d, 2H), 8.1 (d, 2H).

Synthesis of III (Triamine): 200 ml of 1M borane.tetrahydro-furan solution was added to 10.7 g of diamide-amine(II) under a nitrogen atmosphere with stirring. The solution was heated to reflux and the refluxing was continued overnight. The reaction solution was cooled and concentrated. HCl (150 mL) was added to the solution to quench excess BH$_3$. The solution was rotoevaporated to dryness. A sodium hydroxide solution was added until basic and extracted with methylene chloride, dried with magnesium sulfate and filtered. More precipitate formed. The precipitate was filtered off and dried and placed in a vacuum desiccator. The solid was recrystallized in 5M HCl solution and left to cool in the freezer (−25° C.) overnight. A white solid was filtered off, rinsed with cold 5M HCl and dried. IR (KBr pellet): 3474.6 cm$^{-1}$, 3374.6 cm$^{-1}$, 2941 cm$^{-1}$, 1646.5 cm$^{-1}$, 1604 cm$^{-1}$·; 1513.1 cm$^{-1}$, 1349.4 cm$^{-1}$.

Synthesis of HETA2:

Although both HETA2 and LiLo2' can be obtained using the same synthetic procedures starting with the triamine (III), the following method is preferred for preparing HETA2.

Synthesis of IV (Nitro HETA2.Ester): 1 g of triamine (III) was dissolved in _50 ml of a 1:1 mixture of DMF and methylene chloride. 10 ml of triethylamine was added to this reaction mixture. This solution was added to _800 ml of acetonitrile with strong stirring under a nitrogen atmosphere, producing a cloudy solution. This was left to stir at room temperature. The solution was rotoevaporated under vacuum to remove all solvent. 200 ml of absolute ethanol was added to the reaction mixture and hydrogen chloride gas was bubbled through the solution to the point of saturation. The solution was then heated to reflux with strong stirring. This process was continued overnight. The reflux was stopped and the solution was rotoevaporated to an oil. The oil was then dissolved in a saturated solution of sodium carbonate, extracted with methylene chloride, dried with magnesium sulfate and rotoevaporated. This mixture was run down a silica gel column using a methylene chloride solution containing 1% methanol as the solvent mixture for elution. IR (KBr pellet): 1735.9 cm$^{-1}$, 1665.2 cm$^{-1}$, 1600.8 cm$^{-1}$, 1518.6 cm$^{-1}$, 1345.9 cm$^{-1}$, 1193.9 cm$^{-1}$. FAB-MS, M+1, 694.2, Rf=0.66 (0.5% methanol in methylene chloride), 1H NMR 1.3 (t, 9H), 2.8 (s, 10H), 3.1–3.9 (m,20H), 4.2 (q, 6H), 7.8 (d, 2H), 8.2 (d, 2H).

Synthesis of amino-HETA2.ester (V): 1.86 of HETA2-nitro-ester (IV) was dissolved in methylene chloride, added to a stirring solution of ethanol containing 200 mg of 10% palladium on carbon and bubbled with hydrogen gas. Bubbling of hydrogen was allowed to continue for additional 3 hours, and at the end of which TLC analysis showed the presence of an amine group as indicated by a flourescamine positive test. UV analysis also showed the presence of an amino group. The catalyst was filtered off and the solution was rotoevaporated.

Synthesis of isothiocyanato-HETA2.ester (VI): Amino-HETA2.ester (V) was dissolved in 200 ml of methylene chloride and thiophosgene was added this solution under nitrogen atmosphere with stirring. This was left at room temperature to react overnight. Methanol was added to the solution at the end. After −10 minutes, the solution was rotoevaporated. This was dissolved in water saturated with sodium carbonate and extracted with methylene chloride, dried with magnesium sulfate, filtered and rotoevaporated. The product was run down a silica gel column (1–3% methanol in methylene chloride). Fractions showing major spots in TLC due to VI were combined and rotoevaporated.

Synthesis of HETA2 (VII):

HETA2 was obtained from isothiocyanato-HETA2 ester by hydrolysis with HCl using a procedure similar to the one described earlier (Subramanian et al, *Bioconjugate Chemistry*, 3, 248, 1992). NMR (1H) spectral analysis confirmed the hydrolysis of ester groups. The infra red spectral analysis showed the presence of isothiocyanato group. IR (KBr pellet): 3418.2 $cm^{-1}$, 2114.3 $cm^{-1}$, 1735.7 $cm^{-1}$, 1670.3 $cm^{-1}$, 1400.8 $cm^{-1}$, 1215.7 $cm^{-1}$.

This material (HETA2) can also be prepared by base hydrolysis of nitro HETA2 ester(IV), followed by reduction and conversion to isothiocyanate.

Synthesis of LiLo2' (X):

Although both HETA2 and LiLo2 can be obtained using the same procedures, the following method is preferred for preparing LiLo2'.

Synthesis of nitroLiLo2' ester (VIII): 25 g of DTPA dianhydride was added to a stirring solution containing triethylamine (50 ml), dimethylformamide (60 ml) and acetonitrile (50 ml) under a nitrogen atmosphere. After approximately 15 minutes 3.8 g of triamine, III (in 320 mg portions) were added to the reaction mixture every hour. A total of twelve portions were added and the solution was stirred at room temperature. At the end of the reaction, the solution was rotoevaporated until most DMF was removed. The reaction mixture was esterified further by treatment with ethanol.

To the reaction mixture 300 ml of absolute ethanol was added and hydrogen chloride gas was bubbled through the solution to the point of saturation. This was heated to reflux. After _5 hours the reaction mixture was rotoevaporated to an oil. The oil was then redissolved in another _300 ml of ethanol and heated to reflux again. The refluxion was continued overnight. The solution was then rotoevaporated and _200 ml of saturated solution of sodium carbonate was added and the flask strongly shaken until all dissolved. The aqueous layer was extracted with _4 times with methylene chloride, which was dried over magnesium sulfate, filtered and rotoevaporated to an oily solution. This oily solution was run down a silica gel column (1% methanol in methylene chloride). The methanol content was increased very slowly. The fractions showing LiLo2' nitro ester by TLC analysis were combined.

LiLo2' nitro ester (VIII) thus prepared was reduced with palladium on activated carbon using a procedure similar to the one described above. This resulted in the formation of LiLo2' amino ester (IX).

Approximately 860 mg of LiLo2' nitro ester (VIII) was dissolved in 30 ml of absolute ethanol and added to a stirring solution of 300 mg of 10% palladium on carbon bubbled with hydrogen gas in ethanol. Hydrogen gas was continuously added to the solution with strong stirring. After about 2.5 hours absorption spectral measurements showed maximum absorption at 237 nm. The reaction mixture was filtered and rotoevaporated. The TLC analysis showed a single spot that was fluorescamine positive.

LiLo2' (X) was produced from LiLo2' amino ester (IX) by first converting it into an isothiocyanate derivative, followed by conversion to LiLo2' by acid hydrolysis. This could also be done by first hydrolyzing the nitro or aminoLiLo2' ester derivative by base (NaOH) followed by conversion to LiLo2'. A typical acid hydrolysis reaction was carried out as follows. To 73 mg of LiLo2' isothiocyanate ester 2 ml of 1M HCl was added and shaken until totally dissolved. This was left to sit at room temperature. If needed more HCl was added to the mixture and reaction allowed to proceed for additional periods of time. At the end the solution was frozen and lyophilized. The infra red spectral analysis confirmed the presence of isothiocyanate group.

Conjugation of HETA2 and LiLo2' to Proteins:

Chelators such as HETA2 and LiLo2' can be coupled to proteins such as 16.88 by using methods well-known in the art. For example, see Subramanian, R. and Meares, C. F., "Bifunctional Chelating Agents for Radiometal Labeled Monoclonal Antibodies", in 'Cancer Imaging with Radiolabeled Antibodies' (D. M. Goldenberg, Ed.) pp 183–199, Kluwer Academic publishers, Boston, 1990. A typical conjugation reaction involves incubation of the chelate and antibody solution (ratio 100:1 to 1:1) at temperatures ranging from 2° C. to 37° C. for an appropriate period of time (5 minutes to 24 hours or more). The conjugate thus obtained can be purified by gel filtration or ion-exchange chromatography.

Conjugation of HETA2 to 88BV59:

HETA2 was conjugated to monoclonal antibodies such as 16.88 and 88BV59 by incubating the two reactants at temperatures ranging from 2°–37° C. for a period of time ranging from 5 minutes to 48 hours at pH 4–9. At the end of the reaction the HETA2 coupled antibody was purified by size exclusion column chromatography. Other methods such as ion exchange chromatography can also be used. The absorbance of the fractions were measured at 280 nm and the fractions containing MoAb-HETA2 (the antibody conjugate elutes off the column in the first peak when size exclusion chromatography is used) were pooled together and concentrated when necessary. A typical conjugation reaction is given below:

88BV59 (2.5 mL, 9.6 mg/mL) and HETA2 (50 μL, 37.5 mg/mL) were combined together in a phosphate buffered saline solution (0.05M, pH 7.2). The pH of the reaction mixture was adjusted with saturated sodium phosphate solution to a pH of 8.5 to 9.0. The reaction mixture was incubated at 2°–8° C. for about 5 hours. At the end the mixture containing the antibody conjugate was purified by gel filtration chromatography using sephacryl high resolution S-300 column chromatography. The fractions containing the antibody conjugate (88BV59-HETA2) eluted off the column in the first peak. These fractions, identified by absorbance measurements at 280 nm, were combined together and concentrated using amicon/centricon membrane filters to a final concentration of 6.8 mg/mL.

Analysis of 88BV59-HETA2:

The antibody conjugate was further analyzed by HPLC using a Phenomenex SEC 3000 column. The conjugate was found to be essentially pure and free of aggregates. The immunoreactivity of the conjugate was analyzed by an identity assay, wherein the ability of 88BV59-HETA2 to bind to cognate antigen for the antibody was compared to that of unconjugated native antibody 88BV59. Both 88BV59-HETA2 and 88BV59 behaved in a similar way, indicating that the conjugation did not affect the immunoreactivity of the antibody.

Indium-111 Labeling of MoAb-HETA2:

Radiolabeling of the immunoconjugate (e.g., 88BV59-HETA2 and 16.88-HETA2) was performed in an acetate/citrate buffer at pH 5–7 at temperatures ranging from 2°–37° C. for a period of time of 5 minutes to 2 hours. A typical radiolabeling reaction is given below:

To 0.9 mCi of indium-111 chloride (NEN, DuPont) 20 μL of 0.6M sodium acetate and 0.06M sodium citrate buffer solutions were added. To this mixture 0.1 ml of 88BV59-HETA2 solution (6.2 mg/ml) was added and the reaction was allowed to occur at room temperature for about one hour. At the end of the reaction an aliquot of 1 mM DTPA solution was added to the reaction mixture. DTPA was added to scavenge any free unbound or loosely bound indium-111 from the reaction mixture. (The radiolabeling reaction can also be carried out without the use of DTPA solution as a scavenger.) The mixture was passed through a gel filtration column and indium-111 labeled 88BV59-HETA2 eluted off the column (Sephadex G-50 gel filtration column) in the first peak. The fractions were pooled together and analyzed by ITLC using phosphate buffered saline solution, pH 7, as the buffer. The HPLC analysis was performed by using a BioSep SEC 3000 column attached to a radioisotope detector. ITLC analysis after column purification showed that the percentage of Indium-111 bound to 88BV59-HETA2 was 99.5%. HPLC analysis showed the presence of >95% pure 88BV59-HETA2.In(111).

The immunoreactivity of 88BV59-HETA2.In(111) was evaluated by a reactive fraction assay using an affinity column containing sepharose beads covalently coupled to cognate antigen (CTA-1) for 88BV59. The reactive fraction of the radiolabeled antibody bound to the column and the non-reactive fraction washed off the column when 0.05M phosphate buffered saline solution, pH 7, containing 1% BSA was used as the washing solution. By measuring the amount of radioactivity in the wash solution and the affinity column the immunoreactivity of indium-111 labeled 88BV59-HETA2.In(111) was determined. It was found that 83.3% of total radioactivity [88BV59-HETA.In(111)] remained bound to the affinity column. This further confirmed that the use of HETA-2 for attaching indium-111 to 88BV59 does not affect the ability of 88BV59 to bind to antigen to a significant extent.

Stability Studies:

The stability of indium-111 labeled 88BV59-HETA2 was evaluated (a) in phosphate buffered saline solution containing excess DTPA solution, and (b) in normal human serum solution. In both cases the percentage of indium-111 bound to 88BV59 was determined as a function of time using the ITLC method.

(a) To an aliquot of 88BV59-HETA2.In(111), a small amount of 1 mM DTPA solution was added and the mixture was incubated at 37° C. for a period of 6 days.

(b) To a solution containing normal human serum, an aliquot of 88BV59-HETA2.In(111) was added and the mixture was incubated at 37° C. for a period of 6 days.

The results of the stability studies at 37° C. are given in Table 1. These studies show that 88BV59-HETA2.In(111) was stable for well over 6 days at 37° C. in serum, as well as in phosphate buffered saline solution in the presence of excess DTPA solution.

TABLE 1

Stability of Indium-111 Labeled 16.88-LiLo2

| Time | Percent Bound to MoAb | |
|---|---|---|
| | Excess DTPA | in PBS/HSA |
| Day 0 | 98.5% | 99.3% |
| Day 1 | 95.0% | 97.4% |
| Day 2 | 93.7% | 94.2% |
| Day 3 | 91.0% | 96.1% |
| Day 4 | 89.3% | 94.0% |
| Day 7 | 85.4% | 94.3% |

Radiolabeling with Y-90:

Radiolabeling of 88BV59-HETA2 with yttrium was performed using a procedure similar to the above except that 0.1M ammonium acetate solution, pH 5, was used as the buffer in the place of sodium acetate/sodium citrate buffer combination. Y-90 labeled conjugate was purified by G50 gel filtration chromatography, and found to be radiochemically pure and immunoreactive. Stability studies further demonstrated that 88BV59-HETA2.Y(90) was stable in serum for well over 48 hours.

Figure 2:
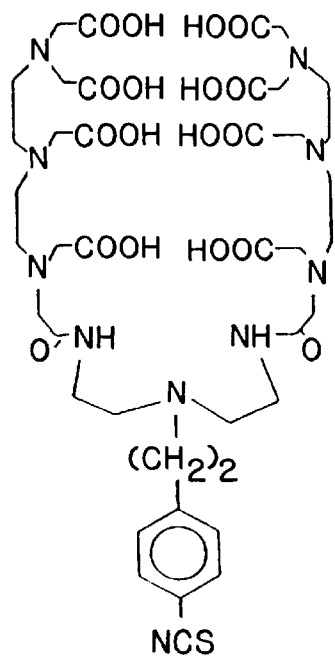
FIG. 2 provides the structure of LiLo2'.
Figure 3:
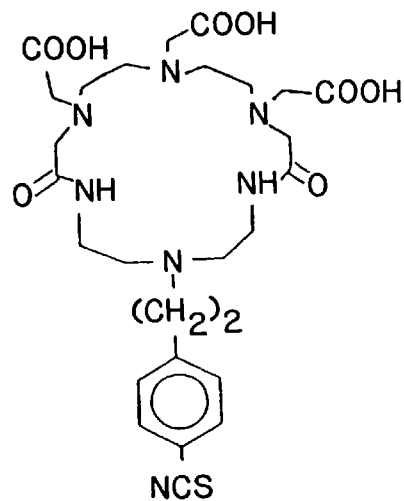
FIG. 3 provides the structure of HETA2.
Figure 4A:
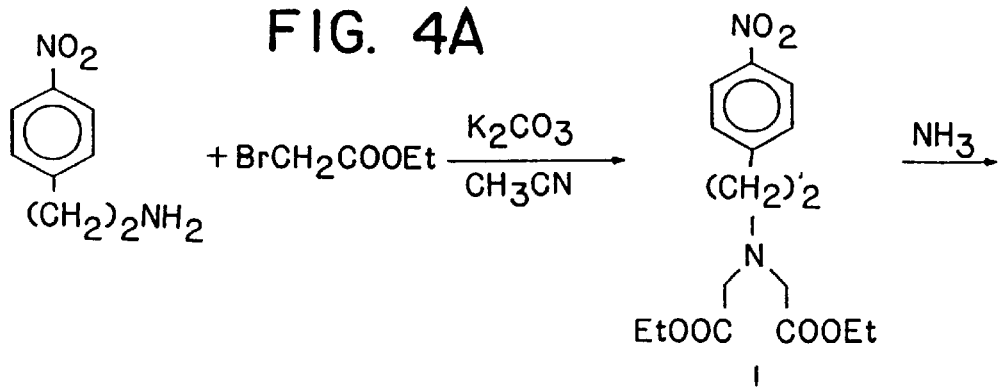
FIG. 4 illustrates the synthetic route employed in the preparation of HETA2 and LiLo2'.
Figure 4A:
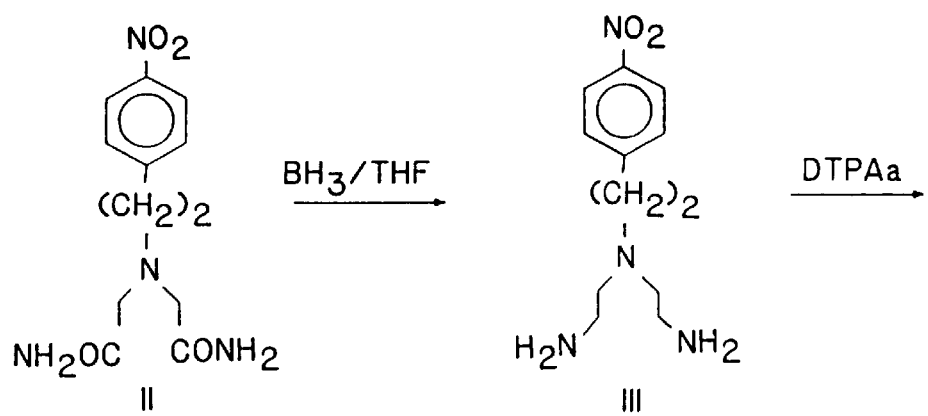
Figure 4A:
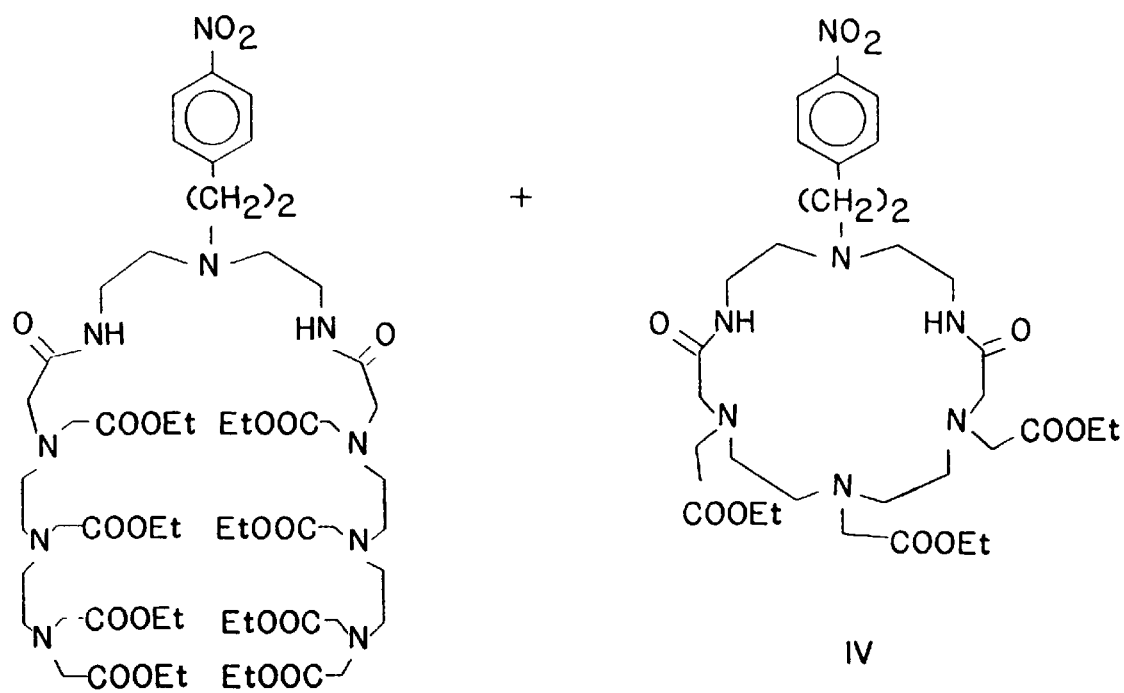
Figure 4B:
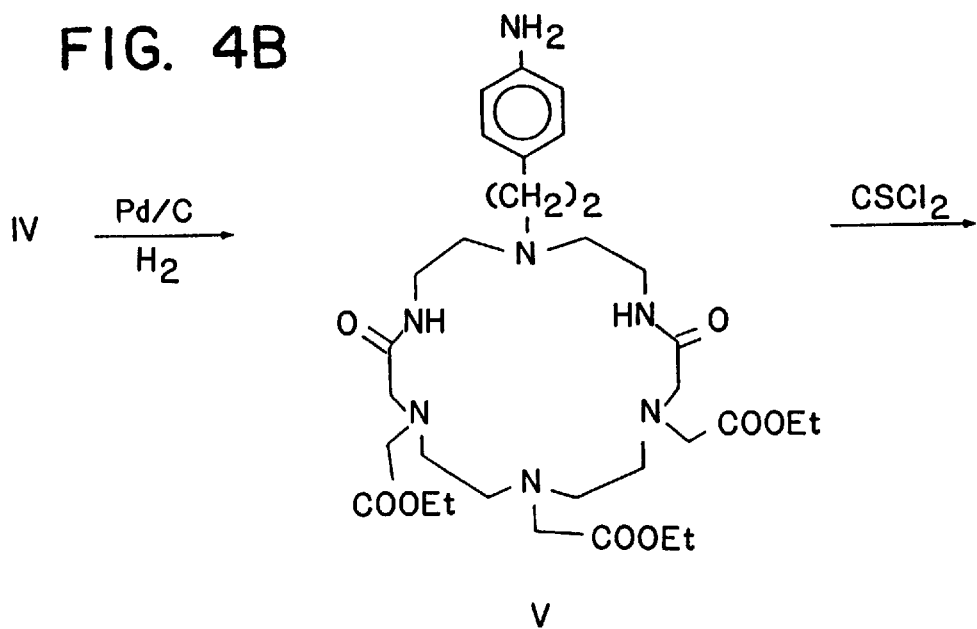
Figure 4B:
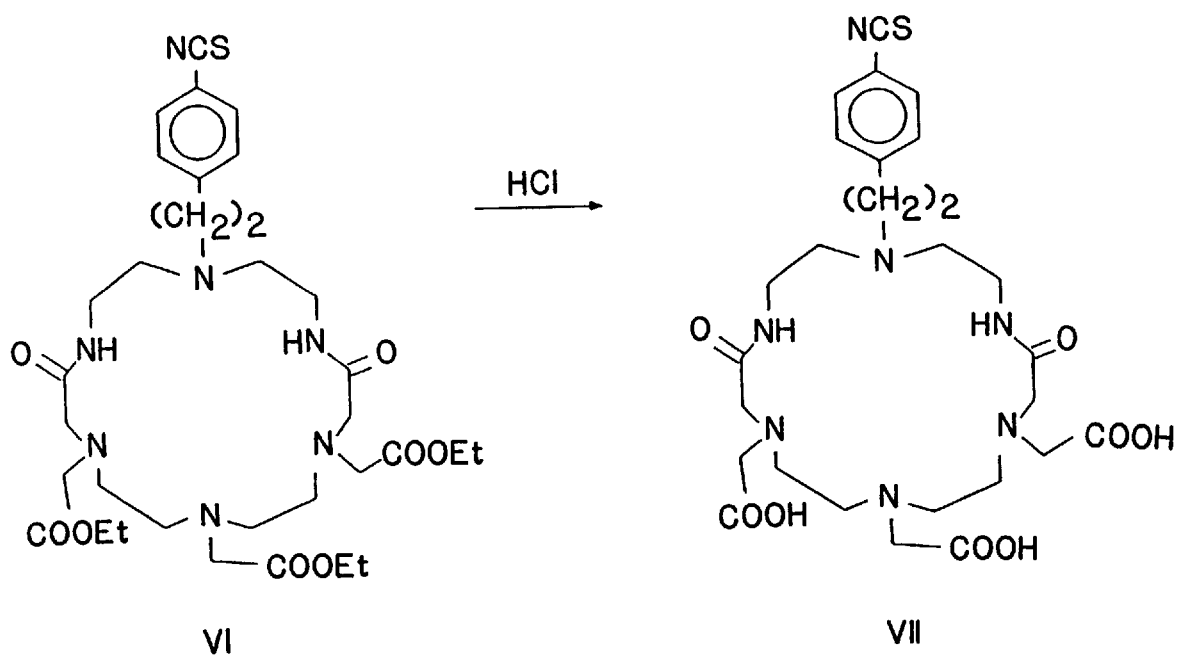
Figure 4C:
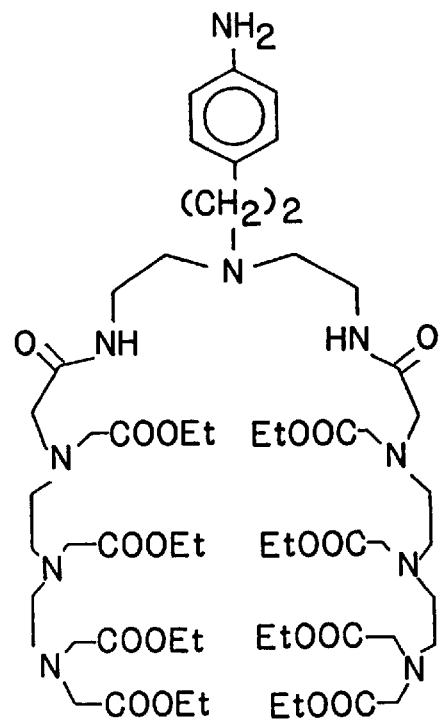
Figure 4C:
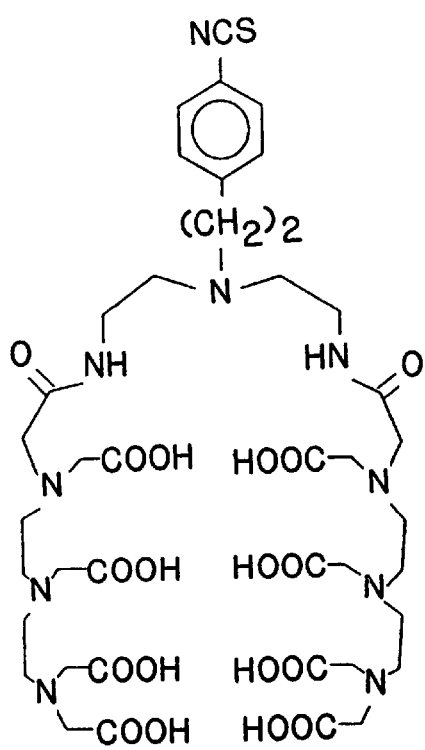
Figure 5:
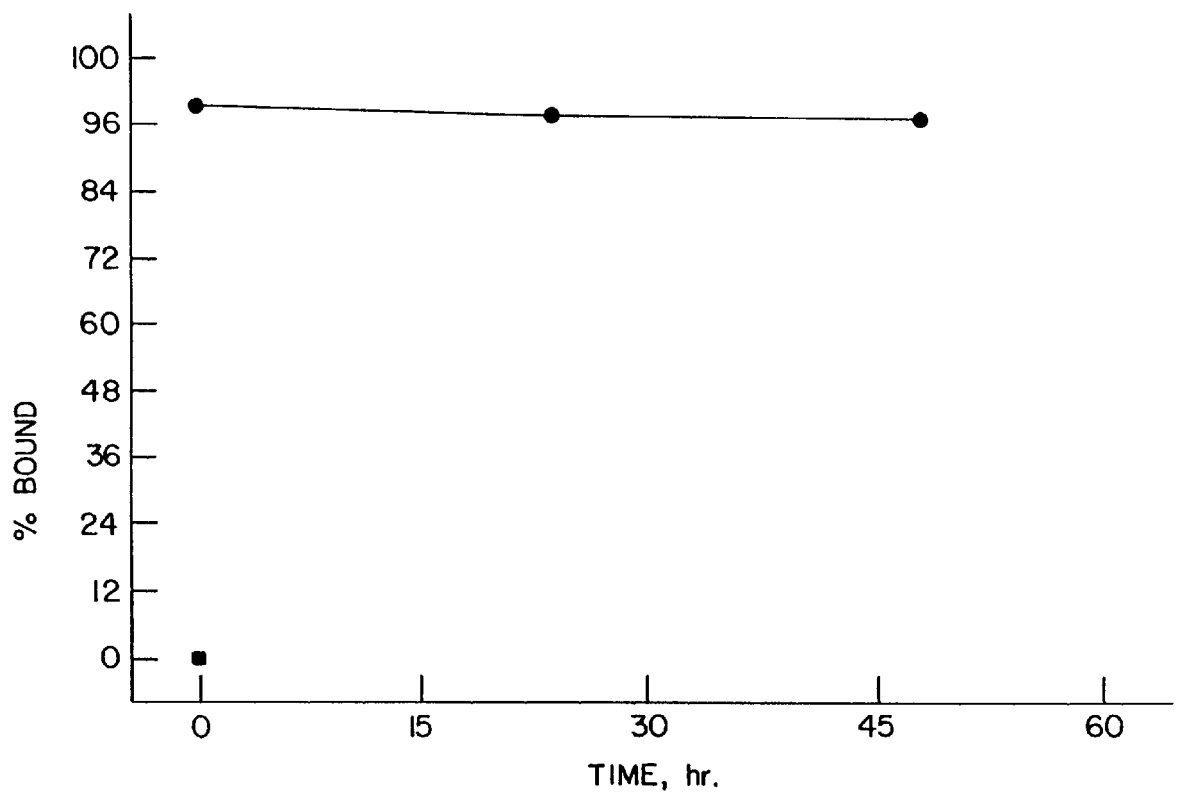
FIG. 5 illustrates the stability of Y(90) labeled 16.88-LiLo2' in human serum. In this figure, the incubation time (37° C.) is plotted against the percentage of Y(90) bound to 16.88-LiLo.

Studies with LiLo2':

LiLo2' was conjugated to 16.88 using procedures similar to those described for the conjugation of HETA2 (see, for example, page 13) and for the conjugation of LiLo to 16.88 in parent application U.S. Ser. No. 08/044,875, which is included herein by reference. In the case of LiLo2' conjugation to 16.88, G-50 sephadex gel filtration chromatography was used for purification. Radiolabeling experiments with indium-111and/or yttrium-90 were performed using procedures described above. Stability of 16.88-LiLo2'.Y(90) in normal human serum is given in FIG. 2. Results of the stability analysis of 16.88-LiLo2'.In(111) are given in Table 2.

TABLE 2

Stability of Indium-111 Labeled 88BV59-HETA2

| Time | Percent Bound to MoAb | | |
|---|---|---|---|
| | Excess DTPA | in Serum | in PBS/HSA |
| Day 0 | 99.4% | 99.8% | 99.7% |
| Day 1 | 97.4% | 98.7% | 98.9% |
| Day 4 | 97.6% | 98.5% | 92.9% |
| Day 6 | 89.9% | 88.0% | 86.8% |
| Day 8 | 89.6% | 81.5% | 81.0% |
| Day 10 | 90.4% | 91.9% | 82.5% |

These experiments show that LiLo2' can be used for attaching radiometals such as indium-111 and yttrium-90 to monoclonal antibodies, such as 88BV59 and 16.88, to form stable radioimmunoconjugates.

These results clearly demonstrate that the polyaminocarboxylate reagents according to the invention, as illustrated by HETA2, and LiLo2', form stable complexes in vivo. These reagents hence are suitable for in-vivo applications.

We claim:

1. A conjugate comprising a polypeptide bound to a chelating agent according to the formula:

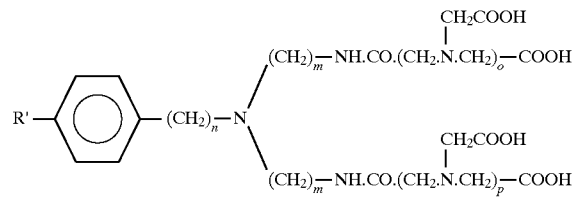

n = 0 to 12
m = 2 to 12
o = 1 to 4
p = 1 to 4
R' = $-CS-NH$, $-CH_2-CO-NH-$, or $-N-N-$ or a bond and when o+p≧3 a closed ring structure may be formed.

2. A compound according to the formula:

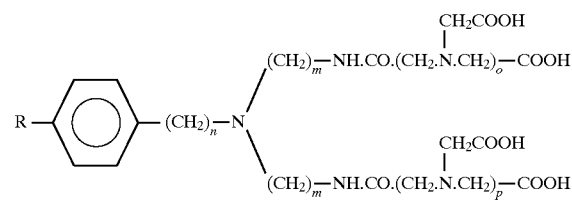

-continued n = 0 to 12
m = 2 to 12
o = 1 to 4
p = 1 to 4
R = —NCS, —NH—CO—CH$_2$—Br or N$_2$Cl and when o+p≧2 a closed ring structure may be formed.

3. The conjugate according to claim 1, wherein the chelating agent is LiLo2':

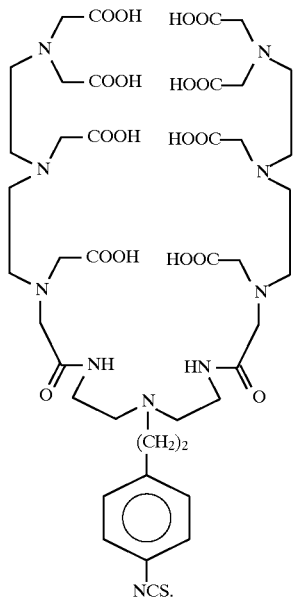

4. The compound according to claim 2, which has the formula:

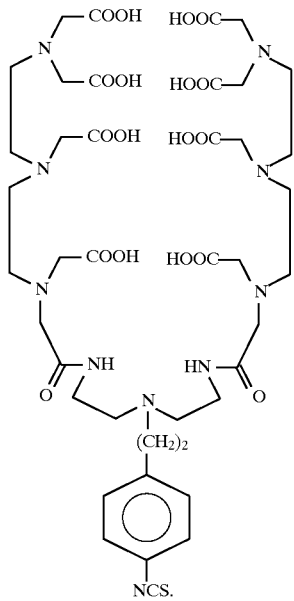

5. The conjugate according to claim 1, wherein the chelating agent is HETA2:

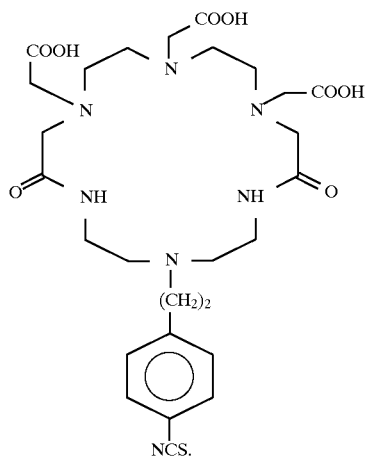

6. The compound according to claim 2, which as the formula:

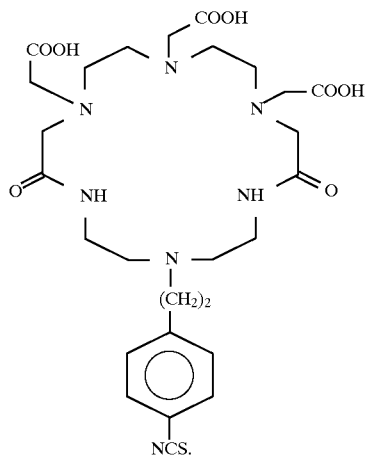

7. A conjugate complex comprising a compound according to claim 2 bound to a metal.

8. A conjugate complex comprising a compound according to claim 6 bound to a metal.

9. A conjugate complex comprising a compound according to claim 6 bound to a metal.

10. A conjugate complex comprising a complex according to claim 1 bound to a metal.

11. A conjugate complex comprising a complex according to claim 3 bound to a metal.

12. A conjugate complex comprising a complex according to claim 5 bound to a metal.

* * * * *